United States Patent
Croitoru et al.

Patent Number: 5,497,441
Date of Patent: Mar. 5, 1996

[54] HOLLOW WAVEGUIDE TIPS FOR CONTROLLING BEAM DIVERGENCE AND METHOD OF MAKING SUCH TIPS

[75] Inventors: Nathan Croitoru, Kfar Saba; Jacob Dror, Tel Aviv; Israel Gannot, Ramat Hasharon; Reuben Dahan, Petach Tikva, all of Israel

[73] Assignee: Ramot University Authority for Applied Research & Industrial Development Ltd., Tel Aviv, Israel

[21] Appl. No.: 271,152

[22] Filed: Jul. 6, 1994

[30] Foreign Application Priority Data

Jul. 9, 1993 [IL] Israel .................................. 106302

[51] Int. Cl.⁶ .................................................. G02B 6/20
[52] U.S. Cl. .................................. 385/125; 385/126
[58] Field of Search .................................... 385/31, 39, 43, 385/88, 125, 901, 902, 126

[56] References Cited

U.S. PATENT DOCUMENTS

| | | |
|---|---|---|
| 3,445,852 | 5/1969 | Karlson . |
| 3,910,678 | 10/1975 | McCartney et al. . |
| 3,926,505 | 12/1975 | Rayces . |
| 4,266,549 | 5/1981 | Kimura ................................ 128/303.1 |
| 4,398,790 | 8/1983 | Righini et al. ....................... 350/96.18 |
| 4,577,936 | 3/1986 | Clegg . |
| 4,652,083 | 3/1987 | Laakmann ............................ 350/96.32 |
| 4,669,818 | 6/1987 | Myer .................................... 350/96.20 |
| 4,671,273 | 6/1987 | Lindsey ................................ 128/303.1 |
| 4,688,892 | 8/1987 | Laakmann ............................ 350/96.32 |
| 4,688,893 | 8/1987 | Laakmann ............................ 350/96.32 |
| 4,693,244 | 9/1987 | Daikuzono .......................... 128/303.1 |
| 4,854,315 | 8/1989 | Stack et al. .......................... 128/303.1 |
| 4,913,505 | 4/1990 | Levy .................................... 350/96.10 |
| 4,930,863 | 6/1990 | Croitoru et al. ..................... 350/96.32 |
| 5,074,861 | 12/1991 | Schneider et al. ........................ 606/17 |
| 5,078,711 | 1/1992 | Kakami et al. .......................... 606/16 |
| 5,119,461 | 6/1992 | Beyer et al. ............................. 385/147 |
| 5,271,077 | 12/1993 | Brockman et al. ....................... 385/31 |
| 5,303,324 | 4/1994 | Lundahl ................................ 385/147 |
| 5,337,381 | 8/1994 | Biswas et al. ........................... 385/36 |
| 5,363,458 | 11/1994 | Pan et al. ................................ 385/31 |
| 5,363,469 | 11/1994 | Elderfield .............................. 385/146 |
| 5,373,571 | 12/1994 | Reid et al. ............................... 385/31 |

FOREIGN PATENT DOCUMENTS

WO91/02562 3/1991 WIPO .............................. A61N 5/06

Primary Examiner—Rodney B. Bovernick
Assistant Examiner—Robert E. Wise
Attorney, Agent, or Firm—Ladas & Parry

[57] ABSTRACT

A hollow waveguide for guiding laser energy, includes a proximal end for receiving the laser energy and a distal end terminating in a distal tip for delivering the laser energy to a working area. The distal end of the hollow waveguide includes an annular, converging, inner surface converging the laser energy towards the distal tip such as to concentrate the laser energy delivered through the distal tip to the working area. Also described are methods of making the hollow waveguide.

20 Claims, 2 Drawing Sheets

HOLLOW WAVEGUIDE TIPS FOR CONTROLLING BEAM DIVERGENCE AND METHOD OF MAKING SUCH TIPS

FIELD AND BACKGROUND OF THE INVENTION

The present invention relates to hollow waveguide tips, particularly for lasers, and also to methods of making such waveguides.

Lasers are now widely used in many surgical procedures, as well as in many industrial applications, for purposes of cutting or vaporizing material in the working area. In many surgical applications of lasers, it is necessary to provide high power density at the working area, e.g., for cutting or ablating tissue. It is also necessary or desirable, in many surgical applications, to deliver the laser energy at different distances from the distal tip of the waveguide without losing substantial power density. However, the laser energy exiting from the conventional waveguide diverges, thereby decreasing the output power density at the working area according to the distance of the working area from the distal tip of the waveguide. Various techniques have heretofore been proposed for concentrating laser energy in the working area, such as lenses, but such techniques are not applicable, or are applicable only with great difficulty, when used with laser waveguides for transmitting relatively high powers.

Recent advances, such as described in our prior U.S. Pat. No. 4,930,863, provide hollow waveguides for delivering laser energy of relatively high power. In such hollow waveguides, however, the laser energy exiting from the waveguide also undergoes a divergence which reduces the power density delivered to a working area as a function of the distance of the working area from the output tip of the waveguide.

OBJECTS AND BRIEF SUMMARY OF THE INVENTION

An object of the present invention is to provide a hollow waveguide which increases the output power density of the waveguide and/or minimizes the divergence of the laser engery outputted from the waveguide. Another object of the invention is to provide methods of making the novel hollow waveguide.

According to the present invention, there is provided a hollow waveguide for guiding laser energy including a proximal end for receiving the laser energy and a distal end terminating in a distal tip for delivering the laser energy to a working area; characterized in that the distal end of the hollow waveguide includes an annular, converging, inner surface converging the laser energy towards the distal tip such as to concentrate the laser energy delivered through the distal tip to the working area.

In one described embodiment, the annular, converging, inner surface ends at the distal tip, such that the inner diameter of the distal tip is smaller than the inner diameter of the hollow waveguide. Such a construction, sometimes hereinafter referred to as a converging-tip construction, provides a high output power density at the distal tip of the waveguide so that even though the laser energy diverges during its passage from the distal tip to the working area, it still has a high power density at the working area.

According to a second embodiment of the invention described below, the hollow waveguide also includes an annular, diverging inner surface between the annular, converging, inner surface and the distal tip for diverging the laser energy before exiting through the distal tip to the working area. In such a construction, sometimes herinafter referred to as a converging-diverging tip construction, the inner diameter of the distal tip of the waveguide is larger than that in the converging-tip construction, but the combination of the converging inner surface followed by the diverging surface minimizes to a substantial extent the divergence of the laser energy exiting from the waveguide, that is tends to collimate the outputted laser energy, so that the output power density changes very little at increased distances of the working area from the distal tip.

The invention also provides methods for making hollow waveguides according to the above constructions.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
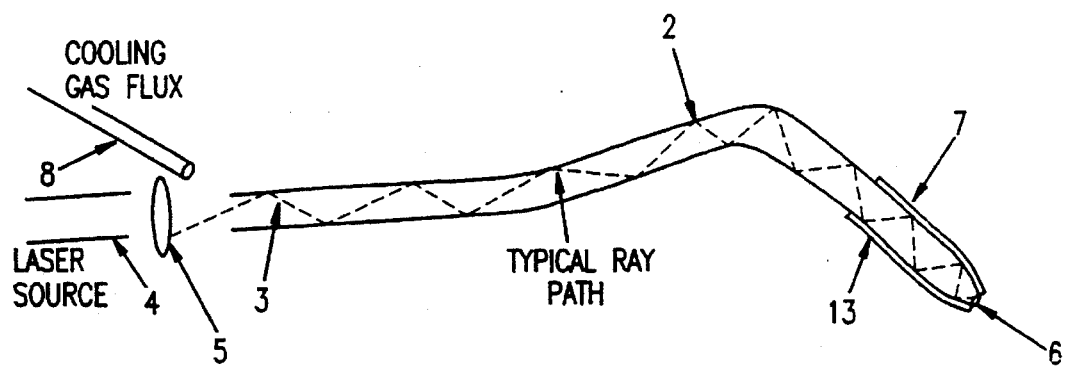
FIG. 1 schematically illustrates one form of hollow waveguide in accordance with the present invention.

FIG. 1 illustrates a hollow laser waveguide 2 for guiding laser energy received at its proximal end 3 from a laser source 4 having a focussing lens 5, and for delivering the laser energy through a distal tip 6 at the distal end 7 of the waveguide to a working area located forwardly of the distal tip. Such a laser system generally includes a source for a cooling gas 8 which gas is fed into a proximal end 3 of the hollow waveguide 2 and exits at the distal tip of the waveguide adjacent to the working area.

Figure 2:
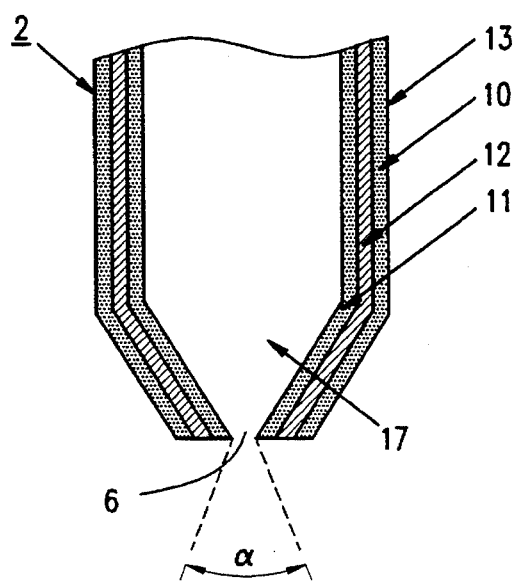
FIG. 2 more particularly illustrates the construction of the distal end of the waveguide of FIG. 1 according to one embodiment of the invention.

The hollow laser waveguide 2 may be constructed as described in our prior U.S. Pat. No. 4,930,863. As shown in FIG. 2, it includes a tube 10, a dielectric layer 11 on its inner surface, and a metal layer 12 between the tube and the dielectric layer. Tube 10 may be of a flexible plastic material such as described in the above patent, but may also be of glass, quartz or metal, e.g., stainles steel, silver, or gold. Preferred examples of such materials are polytetrafluoroethylene for the tube 10, a silver halide, (e.g., silver iodide or bromide) for the inner dielectric layer 11, and silver for the metal layer 12. The outer face of the tube 10 may be coated with a protective layer 13, e.g., nickel, for its complete length, or only at the distal end 7 of the waveguide; the latter is shown in FIG. 1.

In the embodiment illustrated in FIG. 2, the distal end of the hollow waveguide is inwardly tapered to produce an annular, converging, inner surface 17 converging the laser energy towards the distal tip 6 such as to concentrate the laser energy delivered through the distal tip to the working area. In the illustrated construction, the annular, converging inner surface 17 ends at the distal tip 6 such that the inner diameter of the distal tip 6 is substantially smaller than the inner diameter of the hollow waveguide 2. As one example, the outer and inner diameters of the waveguide 2 may be 1.9 mm and 1.05 mm, respectively, and the inner diameter of the distal tip 6 may be 0.75 mm.

It will thus be seen that the construction illustrated in FIG. 2 decreases the size of the laser beam at the distal tip, and therefore increases its power density. However, as soon as the laser beam exits from the distal tip 6, it diverges, as shown by the broken lines in FIG. 2, so that the power density decreases with an increase in the distance from the distal tip to the working area receiving the laser energy.

Figure 3:
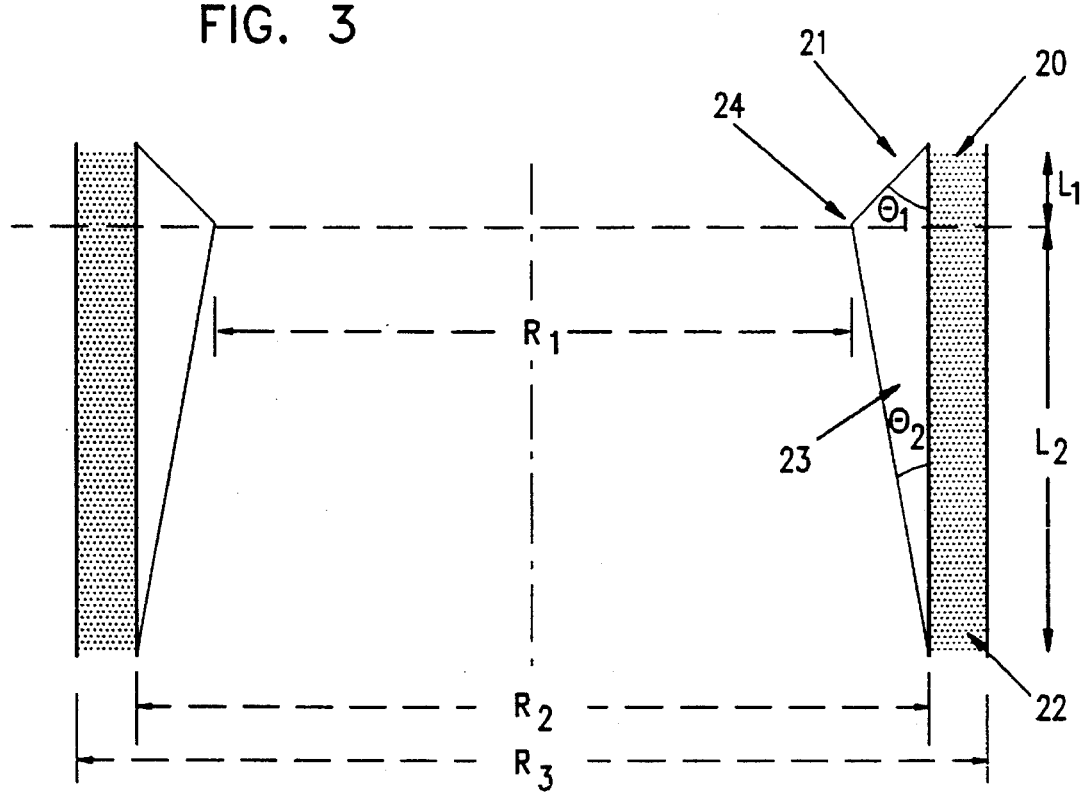
FIGS. 3 and 4 schematically illustrate the construction of distal end of the waveguide of FIG. 1 according to a second embodiment of the invention.
Figure 4:
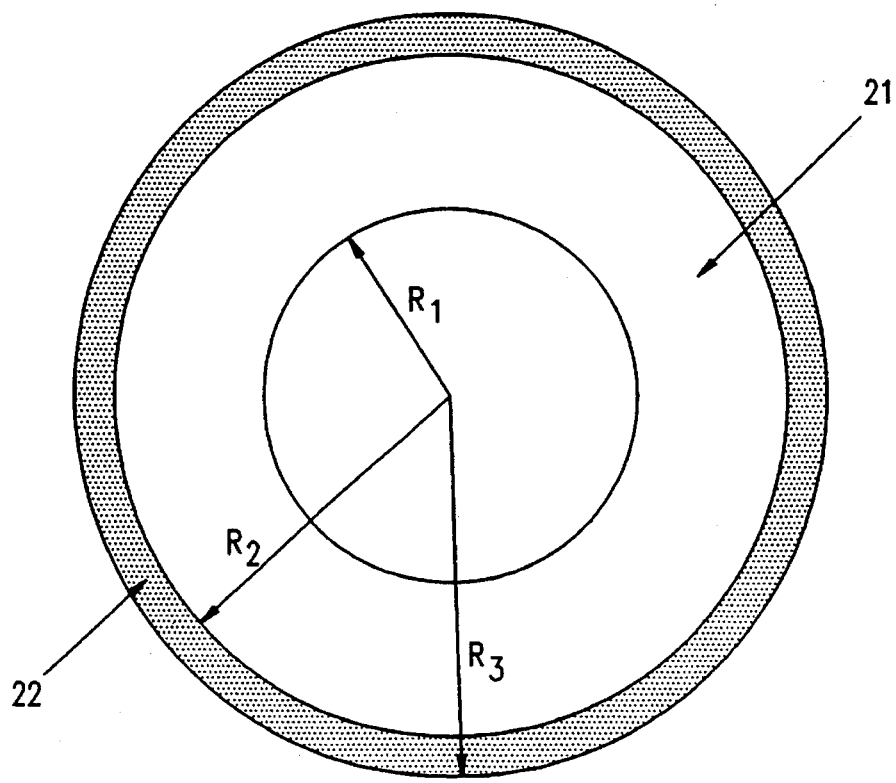

FIGS. 3 and 4 illustrate a construction of the distal end of the hollow waveguide in order to minimize the divergence angle of the laser energy exiting from the distal tip. In this construction, the distal end of the waveguide is formed with an annular, converging inner surface 21, similar to converging surface 17 in the FIG. 2 embodiment, for converging the laser energy towards the distal tip 22. However, the converging surface 21 is immediately followed by an annular diverging inner surface 23 which diverges the laser energy before exiting through the distal tip 22 to the working area. As seen particularly in FIG. 3, the end of the converging surface 21 coincides with the beginning of the diverging surface 23 along annular line 24, which represents the throat or smallest-diameter portion of the distal end of the waveguide.

As can be seen from FIG. 3, the inner diameter at the distal tip 22 of the waveguide is the same as in the inner diameter of the waveguide 20 before formed with the converging inner surface 21. Thus, the diameter of the laser energy exiting from the distal tip 22 is substantially the same as in the hollow waveguide not formed with the converging inner surface 21 (or 17 in FIG. 2). However, the diverging angle of the laser energy exiting from the distal tip 22 is substantially much less, very closely approaching parallelism.

For example, in a hollow waveguide having an internal diameter of 1.05 mm and not formed with either the converging-tip construction of FIG. 2, or the converging-diverging tip construction of FIGS. 3 and 4, the diameter of the laser energy exiting from the distal tip would be 1.05 mm, but the divergence angle ($\alpha$, FIG. 2) would be approximately 6°. When forming the distal tip with the converging-tip construction illustrated in FIG. 2, wherein the inner diameter of the hollow waveguide is 1.05 mm, and the inner diameter of the distal tip 6 is 0.75 mm, the diameter of the laser energy at the distal tip would be 0.75 mm, but the divergence angle ($\alpha$) was found to be 10°. On the other hand, when forming the distal tip with the converging-diverging tip construction of FIGS. 3 and 4, with $R_1$=0.75 mm, $R_2$=1.05 mm, $R_3$=1.5 mm, $l_1$=4 mm, and $l_2$=48 mm, the divergence angle ($\alpha$) was found to be 0.3°; i.e., substantially parallel to the longitudinal axis.

It will thus be seen that the converging-tip construction illustrated in FIG. 2 has the advantage of increasing the power density of the laser radiation at the distal tip as compared to a conventional construction, but the power density decreases at a higher rate with an increase in distance between the distal tip and the working area. In the converging-diverging tip construction of FIGS. 3 and 4, however, the power density of the laser energy at the distal tip is substantially the same as in a conventional construction, but the divergence angle is very substantially reduced so that the power density stays relatively constant with an increase in the distance from the distal tip to the working area. Accordingly, the construction illustrated in FIG. 2 is particularly useful in applications requiring a high power density at or very close to the distal tip; whereas the construction illustrated in FIGS. 3 and 4 is particularly useful in applications requiring either a high power density at a location further from the distal tip or a substantially uniform power density at different distances from the distal tip.

The converging inner surface 17 in the construction of FIG. 2, and the converging surface 21 in the construction of FIGS. 3 and 4, causes a large amount of energy to impinge against these converging surfaces, producing a heat build-up at these surfaces. This may cause the resulting heat to distort the distal tip of the hollow waveguide. This effect can be eliminated or reduced by including the external metal layer 13 over the distal end of the hollow waveguide to improve dissipation of the heat. Such a metal coating may be applied over the complete outer surface of the waveguide, or only the distal end portion of the waveguide.

Figure 5:
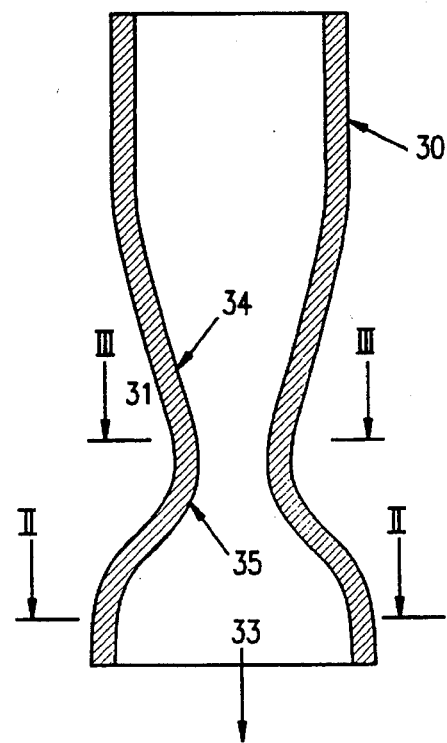
FIG. 5 illustrates one manner of making the distal tip of a hollow waveguide of either the converging-tip construction of FIG. 2, or the converging-diverging tip construction of FIGS. 3 and 4.

FIG. 5 illustrates one manner of making the distal tip of a waveguide according to either the converging-tip construction of FIG. 2, or the converging-diverging tip construction of FIGS. 3 and 4.

The hollow flexible tube 30 may be of polytetrafluoroethylene having an internal diameter of 1.05 mm, and an outer diameter of 1.9 mm. The hollow tube is heated around its circumference at a predetermined location, e.g., by a heating gun, a small circular oven, or a hot water bath, as the two ends of the tube are pulled apart with a force of about 3 Kgm. This causes the tube to assume the stretched configuration illustrated in FIG. 5. If the distal tip is to have the converging-tip construction of FIG. 2, the tube is cut along line II—II; and if the distal tip is to have the converging-diverging tip construction of FIGS. 3 and 4, it is cut along line III—III of FIG. 5.

The inner surface may then be coated with a metal coating (e.g., coating 12, FIG. 2) followed by a dielectric coating (e.g., coating 11, FIG. 2) in accordance with the method described in Patent 86296 (U.S. Pat. No. 4,930,863). The outer surface of the plastic tube, or only its distal end, may be coated with a metal coating (e.g., coating 13 in FIG. 2) in the same manner and at the same time the inner metal coating is applied. The metal coatings may be silver, and the dielectric inner coating may be silver iodide or silver bromide.

Another possible method for making the converging-tip construction of FIG. 2, or the converging-diverging tip construction of FIGS. 3 and 4, is to control the deposition of the metal layer on the inner surface of the hollow plastic tube according to the desired configuration of the distal tip. For example, a distal tip of originally cylindrical configuration can be shaped to produce the configuration of FIG. 2, or the configuration of FIGS. 3 and 4, by controlling the time and/or rate of deposition of the metal coating as the distal tip is moved through a plating bath during a single plating operation, or a plurality of plating operations, to build up the desired converging or converging-diverging shape at the distal end. The metal layer may then be coated with the dielectric layer on its inner surface.

A still further method that may be used is to produce a metal insert of the desired converging or converging-diverging configuration, bond the metal insert to the inner face of the hollow plastic tube, coat the inner surface of the hollow plastic tube and also the metal insert with the metal coating, and then apply the dielectric coating over the inner face of the metal coating.

The invention has been described above with respect to several preferred embodiments, but it will be appreciated that these are set forth merely for purposes of example, and that many other variations, modifications and applications of the invention may be made.

We claim:

1. A hollow waveguide for guiding laser energy including a hollow tube, a dielectric layer on the inner surface of the tube, and a metal layer between said tube and said dielectric layer; said hollow waveguide having a proximal end for receiving the laser energy and a distal end terminating in a distal tip for delivering the laser energy to a working area; said distal end of the hollow waveguide including an annular, converging, inner surface converging the laser energy towards said distal tip such as to concentrate the laser energy delivered through the distal tip to the working area.

2. The hollow waveguide according to claim 1, wherein said tube is a flexible plastic tube.

3. The hollow waveguide according to claim 1, wherein said tube is of glass, quartz or metal.

4. The hollow waveguide according to claim 1, wherein said converging inner surface ends at said distal tip, such that the inner diameter of said distal tip is smaller than the inner diameter of the hollow waveguide.

5. The method of making the hollow waveguide of claim 4, wherein said hollow waveguide is made by a sequence of steps comprising:

heating said hollow tube at a portion thereof adjacent one end thereof;

at the heated portion of the hollow tube, drawing the hollow tube to thereby reduce its diameter;

cutting the hollow tube along its reduced diameter;

and coating the inner surface of the hollow tube first with said metal layer and then with said dielectric layer.

6. The hollow waveguide according to claim 1, wherein at least said distal end of the hollow waveguide includes a metal layer on its outer surface.

7. A hollow waveguide for guiding laser energy, including a proximal end for receiving the laser energy, and a distal end terminating in a distal tip for delivering the laser energy to a working area; said distal end of the hollow waveguide including an annular, converging, inner surface converging the laser energy towards said distal tip such as to concentrate the laser energy delivered through the distal tip to the working area; said hollow waveguide further including an annular, diverging inner surface between said annular, converging, inner surface and said distal tip for diverging the laser energy before exiting through said distal tip to the working area.

8. The hollow waveguide according to claim 7, wherein said diverging inner surface ends at said distal tip of the hollow waveguide.

9. The hollow waveguide according to claim 7, wherein the end of said converging inner surface coincides with the beginning of said diverging inner surface.

10. The hollow waveguide according to claim 7, wherein said distal tip is of substantially the same inner diameter as that of the hollow waveguide.

11. The hollow waveguide according to claim 7, wherein the distal end of the hollow waveguide is shaped to define said annular converging and diverging inner surfaces.

12. The hollow waveguide according to claim 7, wherein said converging and diverging inner surfaces are defined by an insert attached to the distal end of the hollow waveguide.

13. The method of making the hollow waveguide of claim 12, wherein said hollow waveguide is made by a sequence of steps comprising:

preparing said insert to have an outer cylindrical surface and an inner surface including an annular converging section followed by an annular diverging section;

bonding said insert to the end of said hollow tube;

and coating the inner surfaces of the hollow tube and of the insert first with said metal layer and then with said dielectric layer.

14. The hollow waveguide according to claim 7, wherein the hollow waveguide includes a flexible plastic tube, a dielectric layer on its inner surface, and a metal layer between the flexible plastic tube and the dielectic layer.

15. The method of making the hollow waveguide of claim 14, wherein said hollow waveguide is made by a sequence of steps comprising:

heating said hollow tube at a portion thereof spaced from one end thereof;

drawing the hollow tube to reduce its diameter at said heated portion and thereby to produce a converging wall followed by a diverging wall;

cutting the hollow tube along said diverging wall;

and coating the inner surface of the tube first with said metal layer and then with said dielectric layer.

16. The method of making the hollow waveguide of claim 14, wherein said hollow waveguide is made by a sequence of steps comprising:

coating the inner surface of one end of said hollow tube with said metal layer with varying thickness to define an annular converging surface followed by an annular diverging surface;

and coating said inner surfaces with said dielectric layer.

17. A hollow waveguide for guiding laser energy, including a proximal end for receiving the laser energy and a distal end terminating in a distal tip for delivering the laser energy to a working area;

said distal end of the hollow waveguide including an annular, converging, inner surface converging the laser energy towards said distal tip such as to concentrate the laser energy delivered through the distal tip to the working area;

said hollow waveguide further including an annular, diverging inner surface between said annular, converging, inner surface and said distal tip for diverging the laser energy before exiting through said distal tip to the working area.

18. The hollow waveguide according to claim 17, wherein said diverging inner surface ends at said distal tip of the hollow waveguide.

19. The hollow waveguide according to claim 17, wherein the end of said converging inner surface coincides with the beginning of said diverging inner surface.

20. The hollow waveguide according to claim 17, wherein said distal tip is of substantially the same inner diameter as that of the hollow waveguide.

* * * * *